United States Patent [19]

Trehan et al.

[11] Patent Number: 4,668,680

[45] Date of Patent: May 26, 1987

[54] 5-AMINO-6,8-DIFLUOROQUINOLONES AS ANTIBACTERIAL AGENTS

[75] Inventors: Ashok K. Trehan, Ann Arbor; Joseph P. Sanchez, Canton, both of Mich.

[73] Assignee: Warner-Lambert Company, Morris Plains, N.J.

[21] Appl. No.: 808,122

[22] Filed: Dec. 12, 1985

[51] Int. Cl.[4] ................. A61K 31/47; C07D 401/10
[52] U.S. Cl. ................. 514/254; 544/363; 546/156
[58] Field of Search ............ 544/363; 514/254

[56] References Cited

U.S. PATENT DOCUMENTS 3,963,736 6/1976 Nakagome .................. 544/156

FOREIGN PATENT DOCUMENTS 899399 7/1984 Belgium .
0078362 5/1983 European Pat. Off. .
3318145 11/1984 Fed. Rep. of Germany .
0174367 10/1983 Japan ..................... 544/363

OTHER PUBLICATIONS

Wise Antimicrobial Agents and Chemotherapy 4/83, pp. 559–564.

Primary Examiner—Christine M. Nucker
Assistant Examiner—Robert Benson
Attorney, Agent, or Firm—Ronald A. Daignault

[57] ABSTRACT

Novel 7-piperazino and 7-N-methylpiperazino derivatives of 5-amino-1-cyclopropyl-6,8-dihydro-1,4-dihydro-4-oxoquinoline-3-carboxylic acids as antibacterial agents are described as well as methods for their manaufacture, formulation, and use in treating bacterial infections.

4 Claims, No Drawings

5-AMINO-6,8-DIFLUOROQUINOLONES AS ANTIBACTERIAL AGENTS

BACKGROUND OF THE INVENTION

1-Cyclopropyl-6,8-difluoro-1,4-dihydro-4-oxo-quinoline-3-carboxylic acids having a piperazino or an N-methylpiperazino group at the 7-position are known from German Offenlegungschrift No. 3318145 and Belgian Pat. No. 899,399. The compounds are described as broad spectrum antibacterial agents.

5-amino-1-ethyl-6,8-difluoro-1,4-dihydro-4-oxo-7-piperazinyl-quinoline-3-carboxylic acid is described in Japanese Patent Publication No. 58:174,367. Copending U.S. application Ser. No. 770,897 of Aug. 30, 1985, describes a group of 5-amino-1-cyclopropyl-6,8-difluoroquinolones as broad spectrum antibacterial agents. The amino substituents at the seven-position are limited to pyrrolidines and spiroamines.

It was thus surprising and unexpected to discover that the heretofore never described 7-piperazino and 7-N-methylpiperazino derivatives of 5-amino-1-cyclopropyl-6,8-difluoro-1,4-dihydro-4-oxo-quinoline-3-carboxylic acid have not only good broad spectrum antibacterial activity in general but especially better activity against *Pseudomonas aeruginosa*, an important and hard to kill bacteria in antibiotic therapy.

SUMMARY OF THE INVENTION

Accordingly, the present invention is to a compound of the formula

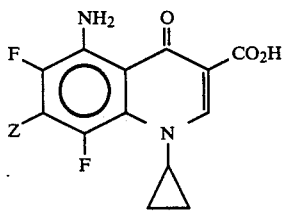

wherein Z is a piperazino or N-methylpiperazino group or a pharmaceutically acceptable acid addition or base salt thereof.

The invention also includes a pharmaceutical composition which comprises an antibacterially effective amount of a compound having structural Formula I and the pharmaceutically acceptable salts thereof in combination with a pharmaceutically acceptable carrier.

The invention further includes a method for treating bacterial infections in a mammal which comprises administering an antibacterially effective amount of the above defined pharmaceutical composition to a mammal in need thereof.

DESCRIPTION OF THE PREFERRED EMBODIMENTS

The compounds of the present invention may be readily prepared by reacting a compound of the formula

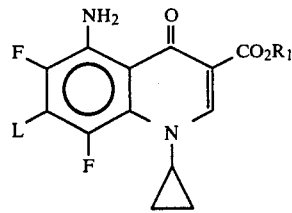

wherein $R_1$ is hydrogen, alkyl of one to six carbon atoms or benzyl and L is fluorine or chlorine with piperazine or N-methylpiperazine, and, when $R_1$ is other than hydrogen, converting by known methods the ester to the free acid, and, if desired, converting by known methods the free acid to a pharmaceutically acceptable acid addition or base salt thereof.

For purposes of this reaction, the piperazines may, if desired, be protected by a group which renders it substantially inert to the reaction conditions. Thus, for example, protecting groups such as the following may be utilized: carboxylic acyl groups such as formyl, acetyl, trifluoroacetyl; alkoxycarbonyl groups such as ethoxycarbonyl, t-butoxycarbonyl, $\beta,\beta,\beta$-trichloroethoxycarbonyl, $\beta$-iodoethoxycarbonyl; aryloxycarbonyl groups such as benzyloxycarbonyl, p-methoxybenzyloxycarbonyl, phenoxycarbonyl; silyl groups such as trimethylsilyl; and groups such as trityl, tetrahydropyranyl, vinyloxycarbonyl, o-nitrophenylsulfenyl, diphenylphosphinyl, p-toluenesulfonyl, and benzyl, may all be utilized. The protecting group may be removed, after the reaction between Compound II and the piperazine, if desired, by procedures known to those skilled in the art. For example, the ethoxycarbonyl group may be removed by acid or base hydrolysis and the trityl group may be removed by hydrogenolysis.

The reaction between the compound of structural Formula II and a suitably protected or unprotected piperazine, may be performed with or without a solvent, preferably at elevated temperature for a sufficient time so that the reaction is substantially complete. The reaction is preferably carried out in the presence of an acid acceptor such as an alkali metal or alkaline earth metal carbonate or bicarbonate, a tertiary amine such as triethylamine, pyridine, or picoline. Alternatively an excess of the piperazine may be utilized as the acid acceptor.

Convenient solvents for this reaction are nonreactive solvents such as acetonitrile, tetrahydrofuran, ethanol, chloroform, dimethylsulfoxide, dimethylformamide, pyridine, picoline, water, and the like. Solvent mixtures may also be utilized.

Convenient reaction temperatures are in the range of from about 20° to about 150° C.; higher temperatures usually require shorter reaction times.

The removal of the protecting group may be accomplished either before or after isolating the product. Alternatively, the protecting group need not be removed.

The starting compounds having structural Formula II are known in the art or, if new, may be prepared from known starting materials by standard procedures or by variations thereof.

Compounds of the Formula II may be prepared by a series of reactions starting with 3,4,5,6-tetrafluoroanthranilic acid. The acid is reacted with acetic anhydride and acetic acid to form 2-acetylamino-3,4,5,6-tetrafluorobenzoic acid. This compound is reacted with oxalyl chloride and dichloromethane in the presence of N,N-dimethylformamide catalyst to form 2-acetylamino-3,4,5,6-tetrafluorobenzoyl chloride. This product is treated with n-butyl lithium and malonic half acid ester to form 2-acetylamino-3,4,5,6-tetrafluoro-β-oxobenzene-propanoic acid ethyl ester.

This product can be converted to 5-acetylamino-1-cyclopropyl-6,7,8-trifluoro-1,4-dihydro-4-oxoquinoline-3-carboxylic acid ethyl ester by a three step reaction. The 2-acetylamino-3,4,5,6-tetrafluoro-β-oxobenzene-propanoic acid ethyl ester is first treated with triethylorthoformate and acetic anhydride. After removal of the solvent the residue is treated with a solution of cyclopropylamine in t-butanol. After the reaction is complete a solution of potassium t-butoxide in t-butanol is added. The resulting product is 5-acetylamino-1-cyclopropyl-6,7,8-trifluoro-1,4-dihydro-4-oxoquinoline-3-carboxylic acid ethyl ester. The ester is hydrolyzed to form 1-cyclopropyl-5-amino-6,7,8-trifluoro-1,4-dihydro-4-oxo-3-quinolinecarboxylic acid.

An alternate pathway to the compounds of Formula II begins with 2-nitro-3,4,5,6-tetrafluorobenzoyl chloride. This starting material is treated with n-butyl lithium and malonic half acid ester to form 2-nitro-3,4,5,6-tetrafluoro-β-oxobenzene propanoic acid ethyl ester. This product can be converted to 5-nitro-1-cyclopropyl-6,7,8-trifluoro-1,4-dihydro-4-oxoquinoline-3-carboxylic acid ethyl ester by a three step reaction. The starting material is first treated with triethylorthoformate and subsequently with cyclopropyl amine in t-butyl alcohol. The product is ring closed with potassium t-butoxide to form 5-nitro-1-cyclopropyl-6,7,8-trifluoro-1,4-dihydro-4-oxoquinoline-3-carboxylic acid ethyl ester. This product is hydrogenated to form the corresponding 5-amino compound. This is then hydrolyzed to form 1-cyclopropyl-5-amino-6,7,8-trifluoro-1,4-dihydro-4-oxo-3-quinoline carboxylic acid.

The compounds of the invention display antibacterial activity as shown in the following table when tested by the microtitration dilution method as described in Heifetz, et al, Antimicr. Agents & Chemoth., 6, 124 (1974), which is incorporated herein by reference. A comparison of the compounds of the present invention to ciprofloxacin, 1-cyclopropyl-6-fluoro-1,4-dihydro-4-oxo-7-piperazinyl-3-quinoline-carboxylic acid, shows clear superiority of the present compounds especially against Pseudomonas aeruginosa and the gram-positive bacteria.

IN VITRO ANTIBACTERIAL ACTIVITY
Minimal Inhibitory Concentration
MIC (μg/ml)

| Organisms | Compound Ex. 1 | Compound Ex. 2 | Ciprofloxacin |
|---|---|---|---|
| Enterobacter cloacae MA 2646 | 0.013 | 0.013 | 0.05 |
| Escherichia coli Vogel | 0.013 | 0.013 | 0.05 |
| Klebsiella pneumoniae MGH-2 | 0.025 | 0.013 | 0.1 |
| Proteus rettgeri M 1771 | 0.05 | 0.05 | 0.1 |
| Pseudomonas aeruginosa UI-18 | 0.025 | 0.1 | 0.4 |
| Staphylococcus aureus H 228 | 0.05 | 0.05 | 3.1 |
| Staphylococcus aureus UC-76 | 0.013 | 0.025 | 0.2 |
| Streptococcus faecalis MGH-2 | 0.05 | 0.1 | 0.8 |
| Streptococcus pneumonia SV-1 | 0.05 | 0.2 | 1.6 |
| Streptococcus pyogenes C-203 | 0.2 | 0.4 | 0.8 |

The compounds of the invention can be prepared and administered in a wide variety of oral and parenteral dosage forms. It will be obvious to those skilled in the art that the following dosage forms comprise as the active component, either a compound of Formula I or a corresponding pharmaceutically acceptable salt of a compound of Formula I.

For preparing pharmaceutical compositions from the compounds described by this invention, inert, pharmaceutically acceptable carriers can be either solid or liquid. Solid form preparations include powders, tablets, dispersable granules, capsules, cachets, and suppositories. A solid carrier can be one or more substances which may also act as diluents, flavoring agents, solubilizers, lubricants, suspending agents, binders, or tablets disintegrating agents; it can also be an encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 to 10 to about 70 percent of the active ingredient. Suitable solid carriers are magnesium carbonate, magnesium sterate, talc, sugar, lactose, pectin, dextrin, starch, gelatin, tragacanth, methyl cellulose, sodium carboxymethyl cellulose, a low melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

Liquid form preparations include solutions suspensions and emulsions. As an example may be mentioned water or water-propylene glycol solutions for parenteral injection. Such solutions are prepared so as to be acceptable to biological systems (isotonicity, pH, etc). Liquid preparations can also be formulated in solution in aqueous polyethylene glycol solution. Aqueous solutions suitable for oral use can be prepared by dissolving the active component in water and adding suitable colorants, flavors, stabilizing, and thickening agents as desired. Aqueous suspension suitable for oral use can be made by dispersing the finely divided active component in water with viscous material, i.e., natural or synthetic gums, resins, methyl cellulose, sodium carboxymethyl cellulose, and other well-known suspending agents.

Preferably, the pharmaceutical preparation is in unit dosage form. In such form, the preparation is subdivided into unit doses containing appropriate quantites of the active component. The unit dosage form can be a packaged preparation, the package containing discrete quantities of preparation, for example, packeted tablets, capsules, and powders in vials or ampoules. The unit dosage form can also be a capsule, cachet, or tablet itself or it can be the appropriate number of any of these packaged forms.

The quantity of active compound in a unit dose of preparation may be varied or adjusted from 1 mg to 100 mg according to the particular application and the potency of the active ingredient.

In therapeutic use as agents for treating bacterial infections the compounds utilized in the pharmaceutical method of this invention are administered at the initial dosage of about 3 mg to about 40 mg per kilogram daily. A daily dose range of about 6 mg to about 14 mg per kilogram is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The following nonlimiting examples illustrate the inventors' preferred methods for preparing the compounds of the invention.

EXAMPLE 1

5-amino-1-cyclopropyl-6,8-difluoro-1,4-dihydro-4-oxo-7-(1-piperazinyl)-3-quinolinecarboxylic acid A suspension of 1.0 g (3.35 mmole) of 5-amino-1-cyclopropyl-6,7,8-trifluoro-1,4-dihydro-4-oxo-3-quinolinecarboxylic acid, 1.15 g (13.4 mmole) of piperazine, 1.36 g (13.35 mmole) of triethylamine and 60 ml of acetonitrile is refluxed for three hours and then stirred at room temperature for 16 hours. The precipitate is removed by filtration, washed with acetonitrile and dried in vacuo at 60° C. to give 5-amino-1-cyclopropyl-6,8-difluoro-1,4-dihydro-4-oxo-7-(1-piperazinyl)-3-quinolinecarboxylic acid, mp 257°–259° C.

EXAMPLE 2

5-Amino-1-cyclopropyl-6,8-difluoro-1,4-dihydro-7-(4-methyl-1-piperazinyl)-4-oxo-3-quinolinecarboxylic acid A suspension of 1.0 g (3.35 mmole) of 5-amino-1-cyclopropyl-6,7,8-trifluoro-1,4-dihydro-4-oxo-3-quinolinecarboxylic acid, 1.36 g (13.35 mmole) of triethylamine and 60 ml of acetonitrile is refluxed for eight hours and stirred at room temperature for 16 hours. The precipitate is removed by filteration, washed with acetonitrile, and dried in vacuo at 45° C. to give 5-amino-1-cyclopropyl-6,8-difluoro-1,4-dihydro-7-(4-methyl-1-piperazinyl)-4-oxo-3-quinoline-carboxylic acid, mp 247°–248° C.

What is claimed is:

1. 5-Amino-1-cyclopropyl-6,8-difluoro-1,4-dihydro-4-oxo-7-(1-piperazinyl)-3-quinolinecarboxylic acid or a pharmaceutically acceptable acid addition or base salt thereof.

2. 5-Amino-1-cyclopropyl-6,8-difluoro-1,4-dihydro-7-(4-methyl-1-piperazinyl)-4-oxo-3-quinoline-carboxylic acid or a pharmaceutically acceptable acid or base salt thereof.

3. A pharmaceutical composition comprising an antibacterially effective amount of a compound of the formula

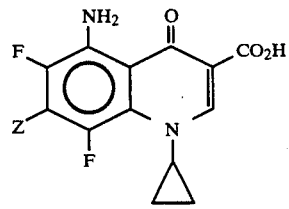

wherein Z is piperazine or N-methylpiperazine, or a pharmaceutically acceptable acid addition or base salt thereof together with a pharmaceutically acceptable carrier.

4. The method of treating bacterial infections in mammals which comprises administering to said mammal a pharmaceutical composition as claimed in claim 3 in unit dosage form.

* * * * *